(12) United States Patent
Stroop

(10) Patent No.: US 11,927,219 B2
(45) Date of Patent: Mar. 12, 2024

(54) BEARING ARRANGEMENT

(71) Applicant: ONDAL MEDICAL SYSTEMS GMBH, Hünfeld (DE)

(72) Inventor: Nicolas Stroop, Fulda (DE)

(73) Assignee: Ondal Medical Systems GmbH, Hünfeld (DE)

( * ) Notice: Subject to any disclaimer, the term of this patent is extended or adjusted under 35 U.S.C. 154(b) by 512 days.

(21) Appl. No.: 17/265,410

(22) PCT Filed: Aug. 5, 2019

(86) PCT No.: PCT/EP2019/071058
§ 371 (c)(1),
(2) Date: Feb. 2, 2021

(87) PCT Pub. No.: WO2020/025834
PCT Pub. Date: Feb. 6, 2020

(65) Prior Publication Data
US 2021/0270323 A1      Sep. 2, 2021

(30) Foreign Application Priority Data

Aug. 3, 2018   (EP) ...................................... 18187397

(51) Int. Cl.
*F16C 41/00*    (2006.01)
*F16D 65/18*    (2006.01)
(Continued)

(52) U.S. Cl.
CPC .......... *F16C 41/001* (2013.01); *F16D 65/186* (2013.01); *H02K 7/102* (2013.01);
(Continued)

(58) Field of Classification Search
CPC ..................................................... F16D 55/14
(Continued)

(56) References Cited

U.S. PATENT DOCUMENTS

| 4,119,013 A | 10/1978 | Seitz |
| 6,305,506 B1 | 10/2001 | Shirai et al. |

(Continued)

FOREIGN PATENT DOCUMENTS

| CN | 2387321 Y | 7/2000 |
| CN | 103573868 A | 2/2014 |

(Continued)

OTHER PUBLICATIONS

English Translation of International Search Report for PCT/EP2019/071058, dated Nov. 8, 2019, 2 pages.
(Continued)

*Primary Examiner* — Melanie Torres Williams
(74) *Attorney, Agent, or Firm* — Seed IP Law Group LLP

(57) ABSTRACT

The invention relates to bearing assembly (10) comprising at least one first bearing element (12) and one second bearing element (14) which are connected together along a longitudinal axis (16) in a rotatable manner relative to each other, wherein the bearing assembly (10) comprises a brake device (18), which inhibits the rotation of the two bearing elements (12, 14) relative to each other by means of a frictional force produced by the brake device (18), and an adjustment device (22), by means of which the brake force which is applied during the rotation the two bearing elements (12, 14) relative to each other can be modified, wherein an adjustment device (22) comprises at least two wedge elements (28, 32), each of which has a wedge surface (34, 36) that rests against each other and which can be moved relative to each other in a sliding manner against each other in order to modify the brake force.

18 Claims, 5 Drawing Sheets

Figure 1:
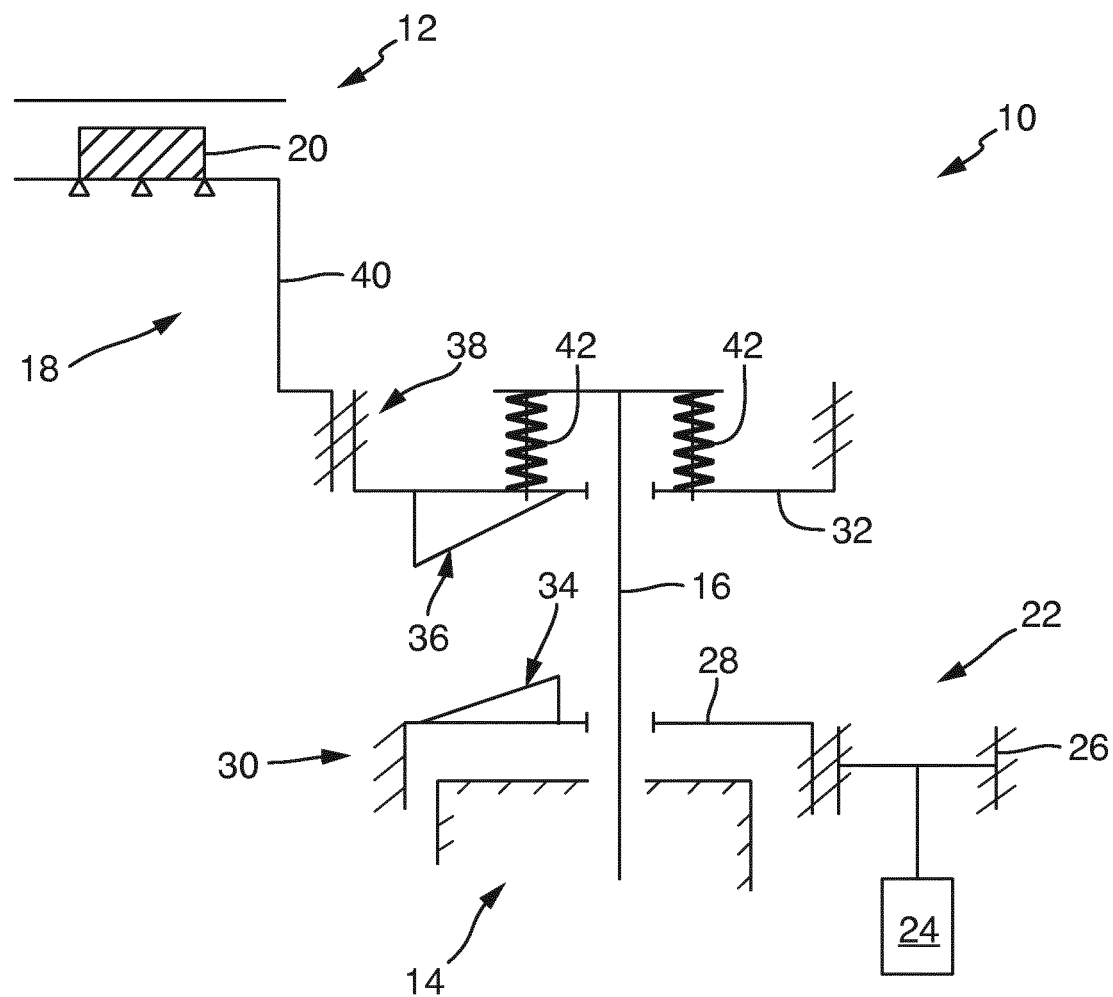

(51) Int. Cl.
*H02K 7/102* (2006.01)
*H02K 7/116* (2006.01)
*A61B 90/50* (2016.01)
*F16D 121/24* (2012.01)
*F16D 125/66* (2012.01)

(52) U.S. Cl.
CPC ........ *H02K 7/116* (2013.01); *A61B 2090/508* (2016.02); *F16C 2361/61* (2013.01); *F16D 2121/24* (2013.01); *F16D 2125/66* (2013.01)

(58) Field of Classification Search
USPC ........................................................ 188/72.2
See application file for complete search history.

(56) References Cited

U.S. PATENT DOCUMENTS

| | | | |
|---|---|---|---|
| 2011/0083927 | A1 | 4/2011 | Herges et al. |
| 2012/0145491 | A1 | 6/2012 | Hyun |
| 2012/0187683 | A1 | 7/2012 | Wohlleb |
| 2015/0075921 | A1 * | 3/2015 | Isono ................... F16D 51/04 |
| | | | 188/72.2 |
| 2015/0308611 | A1 | 10/2015 | Oginski et al. |
| 2017/0114828 | A1 | 4/2017 | Knappe et al. |

FOREIGN PATENT DOCUMENTS

| | | | | |
|---|---|---|---|---|
| CN | 107448520 A | * | 12/2017 | ............. F16D 65/14 |
| DE | 102007003470 A1 | | 7/2008 | |
| DE | 102010005210 A1 | | 7/2011 | |
| DE | 202013001995 U1 | | 7/2013 | |
| EP | 2479428 A1 | | 7/2012 | |
| FR | 2340163 A1 | | 9/1977 | |
| WO | WO-02095257 A2 | * | 11/2002 | ............ B60T 13/741 |
| WO | 2008/148526 A2 | | 12/2008 | |
| WO | WO 2011118630 A1 | | 9/2011 | |
| WO | WO 2014050513 A1 | | 4/2014 | |
| WO | WO 2014095706 A1 | | 6/2014 | |

OTHER PUBLICATIONS

Li-xin., "Latest development of international heavy freight rolling stocks," *Electric Drive for Locomotives* 1(1):1-4, 2002.
European Office Action, dated Apr. 13, 2023, for European Patent Application No. 19 752 999.3-1012, 7 pages.

* cited by examiner

BEARING ARRANGEMENT

The invention relates to a bearing assembly comprising at least one first bearing element and one second bearing element.

In known electromagnetically actuated bearing assemblies, an anchor plate having an attached friction pad is pressed by pretensioned pressure springs against a counter face, for example a pressure plate, in order to inhibit a movement of respective bearing elements to each other. The anchor plate is coupled to a first casing part, which may be denoted as stator, in a rotatably fixed way. The pressure plate is coupled to a second casing part, which may be denoted as rotor, in a rotatably fixed way. The friction pad may here be attached to both the anchor plate and also the pressure plate.

In a braked state, the friction generated by the pressure force of the pressure springs generates a braking torque. The braking torque inhibits any unintentional movement of a carrier arm system, for example, which is held by means of the bearing unit in a movable way at least respectively to one rotational degree of freedom. During an electromagnetic operation of the bearing unit, which may also be denoted as activation, current is applied to a strong electromagnet, which is connected to the stator in a fixed way, for example. The resulting magnetic field acts against the pressure force of the springs and attracts the anchor plate. Thus pressing of the friction pad is ended, and stator and rotor may then be rotated relative to each other using little force. A distinctive feature of this operation principle is that the pressure force, which causes the braking torque, corresponds to the force the electromagnet has to generate for releasing the brake. At a high braking torque, the electromagnet thus has to be dimensioned in a correspondingly strong way, and the currents within a coil of the electromagnet are sufficiently large. In addition, the gap between the electromagnet and the anchor plate is crucial for working at high braking torques, as the magnetic force is considerably reduced when the distance to the magnet increases. This results in high requirements regarding manufacturing accuracy and mounting effort, in particular to keep the gap small. For example, for setting the gap, a fine thread which is complex to manufacture having a small slope between the pressure plate and the casing is provided. Here, after setting the position, the position of the pressure plate at the fine thread is fixed by means of an adhesive which results in a very difficult maintenance.

A further known design solution for setting or braking a bearing unit is the usage of a resilient pressure hose which is expanded by applying a pneumatic interior pressure. Said expansion leads to a pressure force on rotor and stator, and generates a frictional force at the active surfaces which inhibits the rotational movement. The pressure hose may for example also assume the function of the springs and the electromagnet. Detrimental to this solution is that during movement of a carrier arm system which is supported by means of the bearing unit, an abrasive wear on the relatively moved active surfaces of the pressure hose, which is also denoted as pneumatic hose, occurs, when the brake is not released. Said abrasive wear may lead to leaking of the pressure hose, which is also denoted as brake hose. Thus, a durability of the bearing unit may be short, and/or respective maintenance periods may be short. A similar effect may occur by cracks on the respective crimp locations of the resilient hose, on which it is attached. The maintenance of a defect brake hose is a complex service effort.

A third known design solutions for setting or braking a bearing unit is a friction brake unit, which is not releasable. Here, a permanent braking torque between the rotor and the stator is generated, which may not be released by the operator. Usually, the braking torque is selected sufficiently high, thus a movement of the carrier arm system which is supported by the bearing unit is still possible, however unwanted movements are inhibited in an quite reliable way. In some embodiments said braking torque is not adjustable, changes according to the ongoing wear of the frictional surfaces, and becomes then no longer correctable.

The bearing units described above are all characterized by a high plurality of variants of parts and assemblies. This also contributes to the fact that maintenance of said bearing units is expensive and complex.

From DE 10 2007 003 470 A1 a device for controlling a frictional torque of a bearing is known, wherein said device is integrated in a bearing. Said device is comparatively large and requires a high force for setting the brake force.

In DE 20 2013 001 995 U1 a rotation bearing is described. A slotted, wedge-shaped ring is shown, which is contracted in the peripheral direction in order to increase the braking force. Thus, the wedge-shape ring is deformed, but remains unmoved. On the slotted ring a second ring having a wedge-shaped cross-section abuts, which also does not move. Said ring may be formed as not slotted, as otherwise an increase of the brake force would not be possible.

US 2012/0187683 A1 describes a method for attenuation of an oscillation of a drive unit in a wind turbine, and the usage of a brake device. Here, it is specified that the wedge-shaped element is to move radially outside in order to modify a brake force. A wedge-shaped counter face is thus formed by a part which surrounds the wedge-shaped element and in addition has of frictional surface.

CN 2387321 Y describes a bearing assembly.

It is an objective of the present invention to provide a bearing assembly, in which a friction force may be provided by means of an installation space reducing device, and may be adjusted with only little force.

This objective is solved by means of the subject-matter of the independent claim. Advantageous configurations of the appropriate development of the invention are described in the respective dependent claims.

The invention relates to a bearing assembly. The bearing assembly may comprise at least one first bearing element and one second bearing element, which are rotatably connected or coupled relative to each other along a common longitudinal axis. The bearing assembly may comprise a brake device, which inhibits the relative rotation of the two bearing elements to each other by means of a frictional force generated by the brake device. Further, the bearing assembly may comprise an adjustment device by means of which the brake force which acts during the relative rotation of the two bearing elements to each other may be modified. The adjustment device may comprise at least two wedge elements which rest against each other on the respective wedge surfaces which are movable relative to each other by sliding down against each other in order to modify a brake force.

Thus, the wedge elements enable to provide a high transmission (ratio) while at the same time requiring little installation space. This way, the frictional force inhibiting the rotation may be adapted in a particularly simple way. For example, in a high transmission (ratio) or a reduced transmission (ratio) including a small actuation of the adjustment device, the frictional force may be adjusted as a pretension force of a pair of brake surfaces for increasing the frictional force across a high range and/or by using only little force. The wedge elements may thus be very simple design parts, and also be very robust and at the same time may bear high loads. This way, the adjustment device and thus the bearing assembly may be very compact and robust. In particular, the adjustment device having the transmission ratio provided by means of the respective wedge elements, may have a low wear.

The bearing assembly is thus especially suitable for fixing respective carrier arms of device supports in a movable way in order to support medical devices. For example, by using the bearing assembly, a carrier arm of surgery devices may be fixed at a ceiling of a surgery room. By means of the brake device it may thus be prevented that the carrier arm is moving during unintentional contact in an undesired way. At the same time, the brake force may be set due to the adjustment device so that the two bearing elements and thus a carrier arm may still be manually moved by an operator, in particular without using too much force.

The frictional force may be generated for example such, that the brake device presses two frictional surfaces against each other, wherein said frictional surfaces are moved relative to each other during a rotation of the bearing elements relative to each other. Thus a frictional force is generated between the two frictional surfaces, which may inhibit the movement by a feedback. The pressing may here be high to a degree that the frictional force basically fixes the two bearing elements to each other and completely inhibits a movement. Preferably however, the frictional force is sufficiently high that the two bearing elements may still be moved relative to each other. The frictional force inhibiting the movement may also be as denoted as brake force. The bearing assembly may also be denoted as bearing assembly having a frictional brake unit or integrated brake feature. In particular, the brake device may be set by means of the adjustment device and/or is adjustable by the frictional force acting during the movement of bearing elements relative to each other. By means of the adjustment device, for example, the brake device may be disengaged from a flow of force, thus during a rotation of the two bearing elements relative to each other, the frictional force does not inhibit the movement any longer. In this case, the adjustment device may also serve as shiftable coupling. In the disengaged state, for example, a friction acts only due to a respective support of the two bearing elements against each other, for example by rolling and/or sliding of the respective balls of a ball bearing or roller bearing. The brake force or the frictional force this then modified thus that it may be activated and deactivated. Therefore, modification may denote here a releasing/completely disengaging or activating/engaging of the brake.

Alternatively or in addition, also an amount of the frictional force during the movement of the bearing elements relative to each other may be changed by means of the adjustment device. By moving the wedge elements relative to each other, thus respective pairs of friction surfaces may be pressed stronger or less strong against one another. In this case, the modification of the frictional force relates then to the intensity of inhibiting the movement. In this case, the frictional force is adjustable. An adjustable frictional force may also be shiftable in a way that it may be reduced to an extent that it essentially equals zero.

A further advantageous configuration of the bearing assembly provides that the brake device comprises a first frictional surface which rotates with the first bearing element in a rotatably fixed way about the longitudinal axis, and a second frictional surface which rotates with the second bearing element in a rotatably fixed way about the longitudinal axis, wherein the two frictional surfaces are clamped against each other by using a pretension force, and are sliding down against each other during the relative rotation of the two bearing elements relative to each other while generating the frictional force, wherein the adjustment device is configured to adjust said frictional force by moving the wedge elements relative to each other for adjustment of the frictional force and thus to modify the brake force. By using the adjustment device, thus the two frictional surfaces may be pressed against one another stronger or less strong. For example, one of the two frictional surfaces may be arranged on one of the two wedge elements, which is then pressed by moving the two wedge elements stronger or less strong against one of the two bearing elements. Preferably, said wedge element or the complete adjustment device connected to the other of the two bearing elements in a rotatably fixed way. Due to the high possible transmission ratio and the high possible load capacity by the respective wedge elements, thus high pressing may be achieved for a small installation space, thus a high frictional force may reliably be provided even in case of small available friction surfaces. The bearing assembly is thus especially compact and/or may thus provide an especially high bandwidth regarding the intensity of inhibiting the rotation. Rotatably fixed may denote here that a part is co-moved with one of the bearing elements during the rotation thereof about the longitudinal axis, or in case the assigned bearing element does not rotate about the longitudinal axis, said part does also not rotate.

The pretension force presses the respective frictional surfaces preferably in a direction orthogonal to the respective surfaces thereof against each other. The two frictional surfaces are thus preferably aligned parallel to each other. Movement of the two wedge elements towards each other may preferably reduce the pretension force, and a movement of the two wedge elements away from each other preferably increases the pretension force. Thus, the amount of the frictional force may be adjusted respective to the pretension force.

A further advantageous configuration of the bearing assembly provides that the bearing assembly comprises a coupling device which may be adjustable between an open state and a closed state, wherein in a closed state, the brake device is engaged, wherein by a rotation of the two bearing elements relative to each other said rotation is inhibited by the frictional force which is generated by means of the brake device, and wherein in the open state, the brake device is disengaged, whereby the two bearing elements are rotatable relative to each other without being inhibited by the brake device, and wherein the adjustment device is configured to adjust the coupling device between the open state thereof and the closed state thereof by moving the wedge elements relative to each other, and thus modify the brake force. Here, a shiftable friction unit may be achieved by installation-space reducing means. This way, it may be not only a frictional force coupling, but also a coupling in which respective positive fitting elements may be engaged or disengaged by means of the adjustment device. For example, a gearing may be engaged by means of the adjustment device and thus a positive-fit force connection may be formed so that the brake device is engaged in the flow of force between the first bearing element and the second bearing element. On the contrary, the adjustment device may also stop or release said engagement, thus the brake device is disengaged.

In case the bearing assembly comprises a coupling device, the brake device is preferably configured to permanently provide a pretension force for generating the frictional force. Thus, the frictional force may be adjusted independently of the activation or deactivation thereof. This may in particular provide advantages regarding manufacturing tolerances and manufacturing costs. The coupling device and the brake device may be functionally separated, thus the coupling device may be simple and cost-efficient. For example, the coupling device is not to comprise a magnet and a precise manufactured gap, wherein, at the same time, said magnet causes the pretension force for creating the frictional force and/or has to be strong enough in order to release the pretension force. The pretension force may thus be independent from the coupling and the force for actuating it and vice versa.

For setting the frictional force separately from the operating force of the coupling device, the brake device may for example comprise a frictional element and at least one clamping device, by means of which the frictional element is permanently clamped against one of the two bearing elements. In the adjustment device, the wedge elements may slide down against each other and thus change their relative distance, in particular the distance to the centers thereof, whereby a coupling element may be engaged with a corresponding coupling element or whereby such an engagement may be released or disengaged.

A movement of the wedge elements towards each other or away from each other may imply that the wedge elements are in total approaching each other or are moving away from each other. However, it has not to imply that the contact face between the wedge elements is enlarged, or a contact between the wedge elements is released.

A further advantageous configuration of the bearing assembly provides that the adjustment device is configured such that by the relative movement of the wedge elements towards each other, they optionally move towards each other or away from each other in a direction basically parallel to the longitudinal axis. Thus, the bearing assembly may in particular reduce installation space, in particular the radial extension thereof may be especially small. One of the two wedge elements may thus form a front face of one of the two bearing elements and may be arranged thereon, and press against an opposite front face of the other of the two bearing elements in order to provide the frictional force during the rotation relative to each other. Preferably, said wedge element is connected to the bearing element, against which it does not apply a pressure, in a rotatably fixed way.

The movement direction of the respective wedge elements may also correspond to the movement towards and away from each other, that is, in particular in an inclined way thereto, preferably orthogonal. Preferably, the movement direction of the wedge elements in respective plane is basically orthogonal to the longitudinal axis. In particular, the two wedge elements may be rotated about the longitudinal axis to each other in a separate plane, in order to shift the wedge elements away from each other or move them towards each other. This way, the bearing assembly may be particularly compact. Alternatively, also the wedge element, which is not connected to the bearing element in a rotatably fixed way, may be rotated around the longitudinal axis in order to shift the wedge elements away from each other or move them towards each other.

Preferably, the adjustment device is here configured in a way that the respective wedge elements do not protrude or protrude only in an minor extent beyond the outer dimensions of the two bearing elements during the movement thereof relative to each other. Thus, also no additional installation space has to be provided for the wedge elements and the movement thereof. In particular, during a rotation movement of the wedge elements relative to each other about the longitudinal axis, no additional installation space in the radial direction is required, and the bearing assembly may be made especially compact.

In a further advantageous configuration of the bearing assembly, the two wedge elements are formed as identical parts This way, the bearing assembly may be especially cost-efficient, in particular by reducing the variations of the parts and the possible usage of scaling effects for mold parts as wedge elements. Preferably, the two wedge elements are rotated about 180° to each other, are arranged one on the other, in particular by means of respective wedge surfaces which are facing each other and/or contacting each other.

A further advantageous configuration of the bearing assembly provides that the two wedge elements are clamped against each other on the wedge surfaces thereof, in particular by means of at least one spring element. Thus, the two wedge elements are clamped together or are further held in contact on the wedge surfaces thereof, even in case the wedge surfaces slide down against each other such that the two wedge elements are to move towards each other. In particular, this way also a contact against gravity may be ensured, and the bearing assembly or the adjustment device may work independently of its position. By means of the spring element it is inhibited prevented that the two wedge elements lift one from one another, and thus a clearance will be unintentionally generated in the adjustment device. The spring element is thus an especially simple and cost efficient element, in order to ensure this. The spring element may provide that in a braking state, the bearing of the upper wedge element is engaged and/or stays engaged in the gearing of the brake ring.

A further advantageous configuration of the bearing assembly provides that at least one of the two wedge elements is formed as ring element which is arranged for moving the wedge elements relative to each other about the longitudinal axis. Preferably, the two wedge elements are formed as ring element and/or are rotatably fixed around the longitudinal axis. Thus, the bearing assembly may be especially installation space saving, and the wedge elements may be adapted to support themselves very well balanced in any position. In case the two wedge elements are formed as ring elements, they are preferably formed as identical parts in order to save costs. Preferably, the other of the two wedge elements is formed to one of the two bearing elements in a rotatably fixed way or fixed thereon to facilitate the rotation of the two wedge elements relative to each other about the longitudinal axis. Due to the rotation of the wedge elements, the wedge surfaces may slide down against each other and the wedge elements may move towards one another or away from another. Preferably, here the two wedge elements are attached to one of the bearing elements, wherein one of the two wedge elements is arranged movable at least in the axial direction. Preferably, it is not the same wedge elements that is rotatable relative to the longitudinal axis and also axially movable about the longitudinal axis in order to minimize a clearance of an adjustment device and/or reduce a risk of tiling of the two wedge elements against each other. The ring element or the ring elements may last be denoted as lifting disc or lifting discs. By sliding down of the ring elements against each other, a lift may be generated by means of the adjustment device.

Preferably, at least one of two wedge elements comprises a recess and/or a through hole for a wedge portion or the wedge surface of the other of the two wedge elements. In said recess and/or through hole, at least a part of the wedge surface or of a wedge portion of the other wedge element may be received at least in part, in particular in predetermined positions relative to one another. This way, the range of motion of the two wedge elements relative to each other may be especially large, whereby the bearing assembly may also be especially compact. For example, a wedge portion of a ring element may slide into a slit of the other wedge element which is configured as a ring element in a predetermined rotation position of the two ring elements to each other, thus the two ring elements may move very closely towards each other. The recess may also be formed by a wedge portion of the respective wedge element, which may the also be formed as slope.

A further advantageous configuration of the bearing assembly provides that the two wedge elements are attached by means of a common guide to one of two bearing elements. By using a common guide, the number of required parts may be especially low, whereby the bearing assembly may be especially easy to mount and to maintain. Further, the bearing assembly may thus be in particular cost-efficient. Preferably, the guide is formed such that one of the two wedge elements is movably attached to the bearing element, to which it is attached by means of the guide in a rotatably fixed way, but axially movable in the direction of longitudinal axis. Contrary, the other of the two wedge elements may for example rotate in a predefined angular portion relative to the bearing element to which the wedge elements are attached. Thus, a relative movement of the two wedge elements to each other is enabled for changing a distance thereof. The distance may for example relate to a distance of the respective centers of the two wedge elements. A distance should for example not be interpreted regarding a gap or spacing, as the wedge elements preferably stay in contact with the wedge surfaces within the range of motion thereof. The rotatably fixed wedge element is thus preferably fixed to the bearing element in the axial direction along the longitudinal axis in order to reduce a clearance of the adjustment device.

A further advantageous configuration of the bearing assembly provides that the guide preferably comprises of plurality of guide pins which are arranged around the periphery of the guide pins which are formed as wedge elements being formed as ring elements, and one of the two wedge elements is mounted to the guide pins in a rotatably fixed way, but axially movable along the longitudinal axis, in particular by means of the respective through holes which match the guide pins in the cross-section thereof, and the other of the two wedge elements is rotatably fixed to the guide pins relative to the longitudinal axis, in particular by means of the respective elongated holes. Said guide has a simple configuration, which may be especially robust in order to receive high loads and/or to be easy to assemble. Preferably, the elongated holes are formed corresponding to the guide bolts, and allow thus a rotation of one of the two ring elements about 40° to 120° about the longitudinal axis, preferably 60° to 80°, especially preferred about 75°, for example. Preferably, the guide comprises here at least three guide pins which are evenly spaced around the periphery, preferably four guide pins which are evenly spaced from one another around the periphery. This way, a statically defined guide may be easily provided. The number may preferably correspond to a number of the respective wedge surfaces of a respective wedge element. The guide pins here are simple components, in particular different guide elements are not required for the two ring elements. The respective elongated holes may here form an abutment on the respective ends thereof, by means of which the rotation movement of the respective ring may be constrained in a simple way. The guide pins may for example comprise a head portion, in particular on a free end, which also forms an abutment which constraints the axial movement of the ring element which is axially movable along the longitudinal axis. The free end may here correspond to an end opposite to the bearing element to which the guide pins are mounted, for example.

Preferably, also for the bearing assembly the two ring elements are formed as identical parts. For example, each of the bearing elements may comprise through holes corresponding to the guide pins, and also elongated holes. Depending on the arrangement of the ring elements on the guide pins, they are then rotatable about the longitudinal axis, and/or axially movable, and/or rotatably fixed in the longitudinal axis. Preferably, here the respective elongated holes may at the same time serve as receiving portion of the wedge portions of the other ring element in predetermined angular positions. Thus, an additional recess and or through holes may be omitted, whereby the respective wedge elements and thus also the bearing elements may be especially cost-efficient.

The two wedge elements may for example be mold as cost-efficient molded parts. Here, the respective elongated holes and/or through holes may be directly integrated by means of molding, thus an additional reworking is preferably be not required.

In a further advantageous configuration of the bearing assembly, the adjustment device comprises an actuator by means of which the wedge elements are movable relative each other. By means of the actuator, thus a manual operation of the adjustment device may not be required. Instead, the operation may for example be triggered by a sensor signal, for example of a contact sensor and/or by an input device, in particular comprising a button. The actuator may also be denoted as actor. At the same time by means of the actuator a further transmission ratio may be provided, for example, by a transmission of a motor of the actuator and/or a gearing of the actuator with one of the two wedge elements. Due to the high transmission ratio which may thus be provided, standard actuators may be used here, for example, step motors or servomotors. Accordingly, the actuator may also be connected to a sensor and/or a control device in order to be able to provide an automatic modification of a brake force, in particular the frictional force.

For example, the actuator may comprise an electric motor or may be formed of an electric motor, wherein a gear may be arranged, for example, on a transmission output shaft which is arranged in engagement with a corresponding gear portion of a wedge element which is formed as ring element, and may thus rotate said ring element about the longitudinal axis. This way, a further transmission stage is provided. The gear portion on the bearing element may for example be arranged on the outside or inside. In case of an outer arrangement, the actuator is especially easy to mount, and is especially easy to maintain, for example by an arrangement on one of bearing elements also on the outside. In an inner gear portion, the actuator may be also arranged inside, in particular radially inside on one of the two bearing elements. This way, the bearing assembly may be particularly compact. Inside and outside in the present invention may relate to a radial direction relative to a longitudinal axis, for example. Preferably, the gear portion may also be formed as a completely peripheral gear ring of the ring element.

In case identical parts are used as bearing elements including an outer or inner gearing, the ring element which is not engaged with the activator may preferably be engaged with a coupling and/or a frictional element of the bearing assembly. This way, said bearing element may be brought into engagement or released from engagement during a relative movement of the two ring elements to each other in order to thus adjust the frictional force, and to engage or disengage the brake device at the same time.

For example, the adjustment device may also be configured to adjust a pretension force for creating the frictional force on a first partial path for adjusting a pretension force, and on a further partial path to adjust the coupling device from the open to the closed state and vice versa. Thus, the adjustment device may advantageously be used for adjusting the operation force and also for operating the coupling device.

A further advantageous configuration of the bearing assembly provides that at least one of the wedge elements comprises a gearing which engages with the corresponding gearing of the actuator for moving said wedge element.

Further features of the invention become apparent from the claims, the exemplary embodiments and the figures. The features and the combination of features mentioned in the specification above and the features and combinations of features mentioned in following exemplary embodiments may be used not only in the respective specified combination, but also in other combinations within the scope of the invention.

HERE SHOWS

Figure 2:
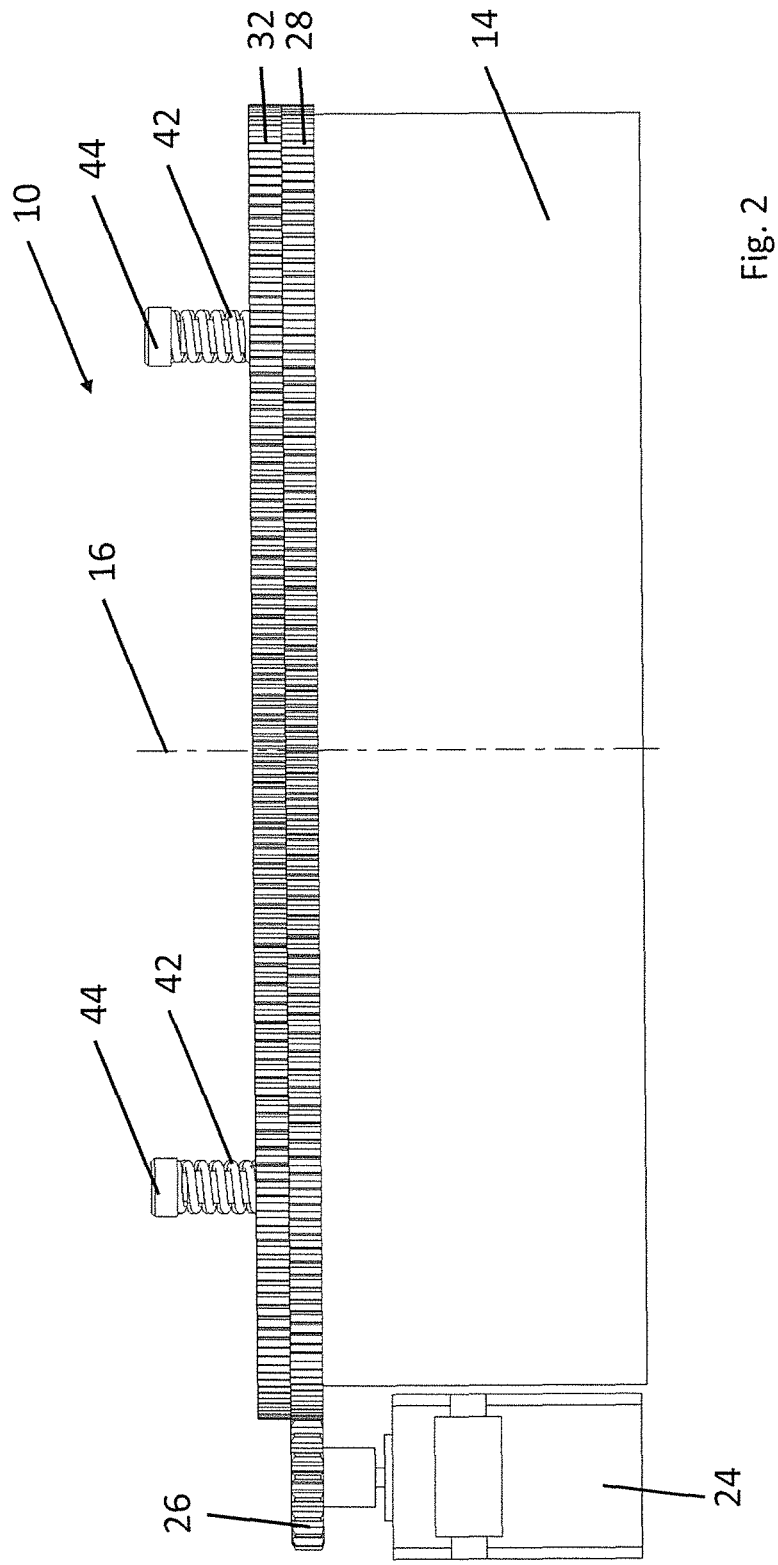
Figure 3:
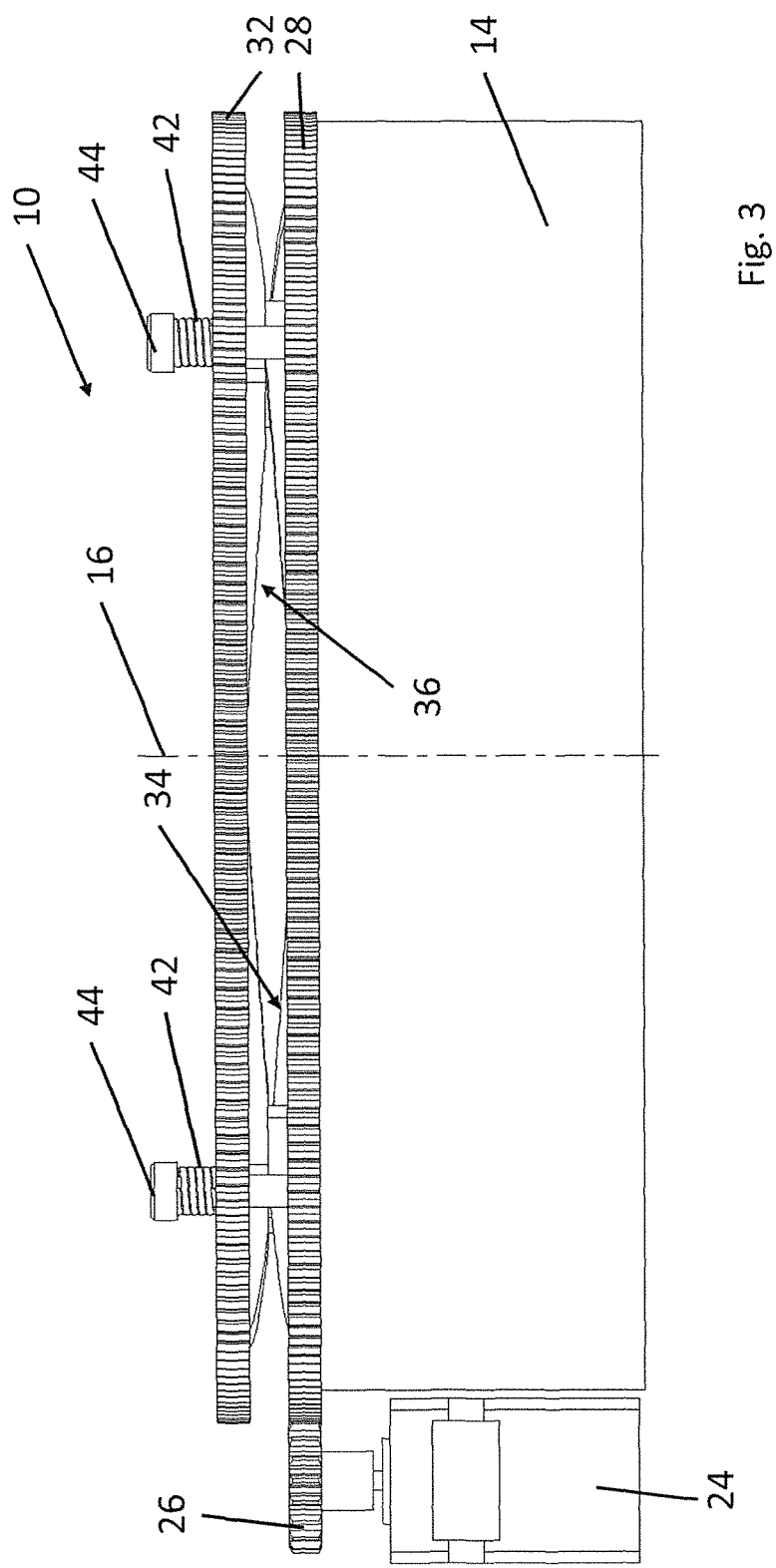
Figure 4:
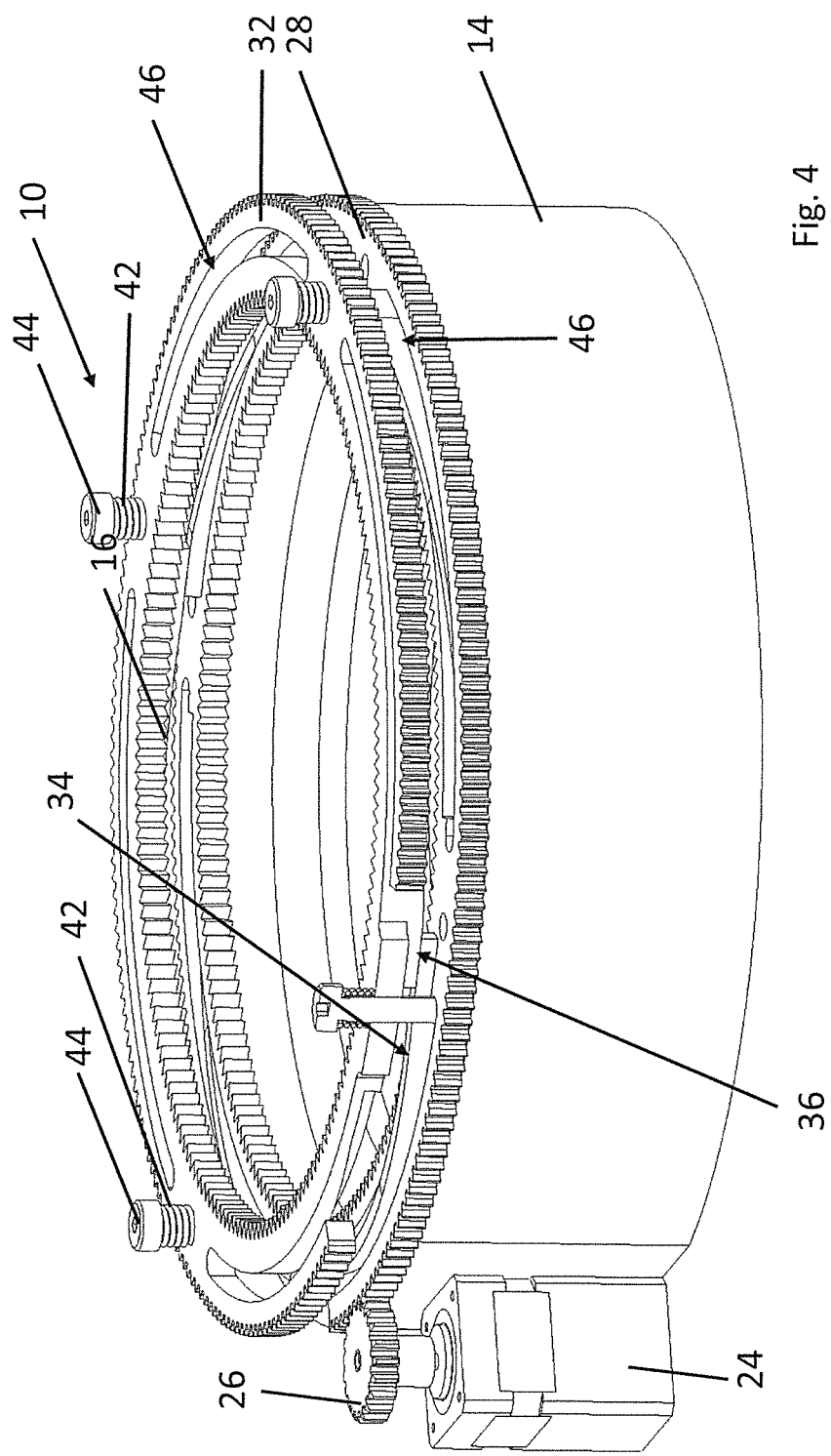
Figure 5:
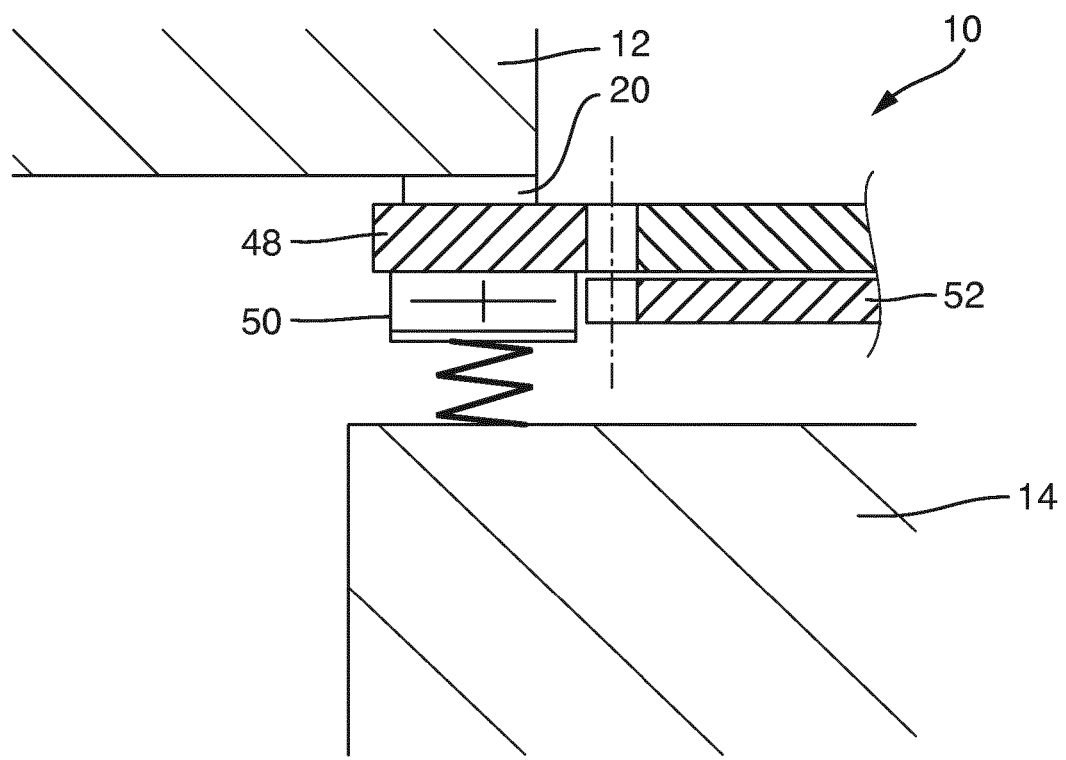

FIG. 1 in a schematic view a schema of a bearing assembly comprising an adjustment device including two wedge elements which rest on the respective wedge surfaces against each other;

FIGS. 2 and 3 in a schematic side view a part of the bearing assembly according to FIG. 1;

FIG. 4 in a schematic perspective view of the bearing assembly according to FIG. 2 and FIG. 3, the respective wedge surfaces of wedge elements, wherein the representation is partly sectioned; and FIG. 5 in a schematic section view a further embodiment of the bearing assembly according to FIG. 1.

FIG. 1 shows a schema of a bearing assembly 10 including a first bearing element 12, which is formed as stator, and a second bearing element 14, which is formed as a rotor. The two bearing elements 12, 14 may rotate relative to each other about the longitudinal axis 16. For example, the bearing assembly 10 is especially suited for rotatably fixing a carrier arm, on which respective medical devices may be supported.

The bearing assembly 10 comprises here a brake device 18, which inhibits or is able to inhibit the relative rotation of the two bearing elements 12, 14 to each other by means of a frictional force generated by the brake device 18. Therefore, a frictional element 20 is pressed against the surface of the first bearing element 12, whereby a frictional force is generated during rotation of the bearing elements 12, 14, which acts against the rotation. Hereto, the frictional element 20 is rotatably fixed to the second bearing element 14.

In the present configuration, the frictional force may here be adjusted by means of the adjustment device 22. Hereto, the adjustment device 22 comprises an actuator 24 which is engaged with a first wedge element 28 by means of a gear 26. Hereto, the first wedge element 28 comprises a radially outer gearing 30 which engages with the gear 26. This way, transmission is performed from the output shaft of the actuator 24 via the gear 26 to the wedge element 28. In the present configuration, the wedge element 28 is thus formed as ring element or disc, which includes a plurality of wedge surfaces 34 on the side thereof facing the other wedge element 32. The second wedge element 32 which is arranged oppositely, is here formed as identical part and thus formed identical to the first wedge element 28, and is also arranged facing the first wedge element 28 with the respective wedge surfaces 36 thereof. The wedge element 32 is just arranged relative to the wedge element 28 rotated by 180°. Although in the present configuration, the two wedge surfaces 34, 36 are shown as being spaced from each other in FIG. 1, they are in abutment. For example, the wedge surfaces 34, 36 are arranged as a plurality of wedge portions along the periphery of the two wedge elements 28, 32, which are configured as discs or ring elements, and thus are also formed in a curved manner corresponding to the periphery. In particular, on each of two wedge elements 28, 32 four wedge surfaces 34, 36, which may be identical, may be arranged evenly spaced along the periphery. The wedge elements 28, 32 include then a fourfold rotational symmetry regarding the longitudinal axis 16, for example.

Further, the wedge element 32, which is shown in FIG. 1 as upper wedge element 32, is coupled to a brake ring 40 by means of the gearing thereof, to which the frictional element 20 is attached. The upper wedge element 32 is thus coupled to a rotor or the second bearing element 14 in a rotatably fixed way, thus the frictional element 20 is also rotating together with it.

For modification of the brake force, the lower wedge element 28, shown in FIG. 1, may be rotated about the longitudinal axis 16 by means of the actuator 24, whereby the two wedge surfaces 34, 36 slide down against each other. This is for example especially clearly shown in the schematic perspective view of said wedge surfaces 34, 36 in FIG. 4. During a rotation of the wedge element 28 about the longitudinal axis 16 in one direction, thus the two wedge elements 28, 32 move towards each other, and during a rotation in the opposite direction, the two wedge elements 28, 32 move away from each other. Correspondingly, the brake ring 40 and the frictional element 20 may also be moved along the longitudinal axis 16. The gearing 38 may be formed correspondingly for transfer of the movement. During the movement of the two wedge elements 28, 32 away from each other, the frictional element 20 is thus moved upwards in FIG. 1, and is thus pressed stronger against the first bearing elements 12 or the stator. Due to said increase of the pressing pressure, a higher frictional force results during a rotation of bearing elements 12, 14 relative to each other about the longitudinal axis 16. On the opposite, during a movement of the two wedge elements 28, 32 towards each other, the pressing pressure of the frictional element 20 against the first bearing elements 12 is reduced, thus a lower frictional force may be defined. Subsequently, this results in a smaller brake torque.

In order to provide an especially small clearance in the adjustment device 22 and/or to enable the movement of the two wedge elements 28, 32 independent of a spatial position of the bearing assembly 10, the upper wedge element 32 is clamped axially along the longitudinal axis 16 against the lower wedge element 28 by means of the respective spring elements 42. The spring elements 42 are for example pressure springs. This way, the two wedge surfaces 34, 36 reliably contact each another. In particular, in case the two wedge elements 32, 28 are moved towards each other, the pressure springs 42 may reliably keep the two wedge elements 28, 32 in contact.

The respective spring elements 42 are thus arranged with the respect center axis above the respective guide pins 44 by means of which the two wedge elements 28, 32 are guided. Said guide is in particular clearly shown in FIGS. 2 to 4. Here, the respective guide pins 44 are evenly spaced around the periphery of the two ring-shaped wedge elements 28, 32.

In the upper wedge elements 32, thus the guide pins 44 are received in the respective through holes, the diameters of which correspond to the diameters of the guide pins 44. Thereby, the upper wedge elements 32 is connected to the rotor or the second bearing element 14 in a rotatably fixed way relative to the longitudinal axis 16, at least in the exemplary embodiment shown in FIGS. 2 to 4. However at the same time, the upper wedge element 32 may be axially moved along the longitudinal axis 16 along the guide pins 44 in order to be able to move the two wedge elements 28, 32 towards each other and away from each other.

Contrary hereto, at the lower wedge element 28, the guiding pins 44 are received in the respective elongated holes 46, thus the lower ring or wedge element 28 may be rotated about the longitudinal axis 16 in a range of motion predefined by the respective elongated holes 46 relative to the second bearing element 14 and also to the upper wedge element 32. For example, the rotational range is 75°, before the respective end portions of the respective elongated holes 46 abut on the guide pins 44.

In FIG. 2, two wedge elements 28, 32 are shown in a posture in which they are utmost moved towards each other. The two wedge elements 28, 32 abut here basically planar on each other. Thus, the lowest possible pressure force of the friction element 20 is set at the first bearing element 12. For example, the friction element 20 may not be in contact with the first bearing element 12 at all, thus the two bearing elements 12, 14 may be rotated to each other essentially without friction around the longitudinal axis 16.

Contrary in FIG. 3, the two wedge elements 28, 32 are shown in a position in which they are lifted one from the other to a maximum and are thus moved away from each other. The two wedge elements 28, 32 may correspondingly also be noted as lifting discs, as they transform a rotation relative to each other about the longitudinal axis 16 in a lift. Here, the two wedge surfaces 34, 36 have slid down against each other such that they essentially rest on each other only at the highest portions. This may in particular be seen in the partly sectioned view of FIG. 4. Correspondingly, as is shown in the view according to FIG. 1, for example, the frictional element 20 is also lifted upwards to a degree that it is pressed against the first bearing element 12 at maximum. Said pressure force may be basically so high that the two bearing elements 12, 14 are essentially rotatably fixed to each other around the longitudinal axis 16.

Due to the structure of the bearing assembly 10, there are three transmission stages which are shifted one after the other. The first transmission stage is a gear transmission of the actuator 24, for example of the electric motor mounted therein. The second transmission stage may for example be provided between the driving gear 26 and the lower wedge element 28, which may also be denoted as lower lifting disc. A third transmission stage and thus an increase of the force results from the wedge surfaces 34, 36 which slide down against each other. A complete transmission is for example obtained by multiplication of the three single transmissions. The actual lifting force for setting the brake force or for an alternative or additional disengagement from the gearing 38 with the brake ring 40, is for example calculated by $F_H = M_{GA} * i_R * i_H / r_{Keil}$, wherein $M_{GA}$ is the gear unit output moment, $i_R$ is the transmission ratio between the gear and the lower lifting disc, $i_H$ is the force increase of the wedge surface, and $r_{keil}$ is the radius of the area of the circle. Frictional impacts are not taken into consideration in said equation. The increase may be high to such a degree that for example also the upper lifting disc or the upper wedge element 32 may be directly used for generating the frictional force or the brake force without any additional provision of the frictional element 20. Here, the two wedge elements 28, 32 may be formed of metal, for example.

As in particular shown in FIG. 4, the two wedge surfaces 34, 36 are formed in one half below and the other half above the planar surface, which faces the respective other of the wedge element, of the remaining wedge element 28, 32 or the respective ring portions thereof. Thus, the wedge surface 36 may slide down by means of the protruding portion thereof on the portion of the wedge surface 36, which is disposed below the planar plane of the lower wedge element 28, thus the two wedge elements 28, 32 may essentially rest against each other by means of the ring portions thereof. Thus, the adjustment device 22 may in particular save installation space.

Alternatively or in addition, the adjustment device 22 may also be used to disengage the brake device 18 from a force path between the two bearing elements 12, 14. Thereto, the gearing 38 may be configured to release the engagement during an axial shift.

A disengagement operation of the present brake device 18, in particular of the brake device 18 shown in FIG. 1, may thus be formed as follows: The actuator 24 is energized, and causes a rotation movement on the drive shaft thereof. An upstream motor transmission increases the torque, as required. On the transmission output shaft a gear 26 is mounted, which teeth are engaged with the outer gearing 30 of the lower lifting disc 28. As the diameter of the drive gear 26 is significantly smaller than the diameter of the lifting disc 28, the torque is again increased, and the rotational speed is thus reduced. The wedge surfaces 34 of the lower lifting disc 28 are here arranged in a way that the wedge surfaces 34 extend upwards. In an upper side of an outer bearing ring, the guide pins 44 adapted as fitting bolts are mounted, which serve for guiding the two lifting discs 28, 32. The upper lifting disc 32 is thus guided by means of the fitting bolts in a way that it is supported in a rotatably fixed way, but may be axially shifted. Here, the pressure springs 42, which press the upper lifting disc 32 against the lower lifting disc 28, act between the upper side of the upper lifting disc 32 and the bolt head of the fitting pins 44 or the guide pins 44. In an engaged state, the gearing 38 of the upper lifting disc 32 is engaged with the respective gearing of the brake ring 40. In case, the lower lifting disc 28 is rotated by the actuator 24, the wedge surfaces 34, 36 slide down against each other. The upper lifting disc 32 is moved upwards by the spring force of the pressure springs 42, and slides off the gearing of the brake ring 40. Here, the brake effect is canceled, thus the adjustment device 22 acts as a coupling.

Contrary to the exemplary embodiment described above, in which the adjustment device 22 serves only for adjusting the frictional force created during rotation of the two bearing elements 12, 14 to each other, here the gearing 38 may thus be released by means of the adjustment device 22, and thus the brake device 18 may be disengaged. The brake effect is also canceled, as the second bearing element 14 is disengaged from the brake ring 40.

In said exemplary embodiment, the pretension force of the frictional elements 20 may be provided separately from the adjustment device 22, for example by a clamping element and/or a further adjustment device including wedge elements.

In case, the brake effect has to be restored, the actuator 24 sets the lower lifting disc 28 back by using the same angle. The upper lifting disc 32 is thus correspondingly pressed downwards by the spring force. The gearing 38 of the upper lifting disc 32 may thus rest on the gearing of the brake ring 40, and automatically engages again during a only very small movement of a carrier arm system which is mounted on the bearing assembly 10, and thus a rotation of the bearing elements 30 12, 14 relative to each other. This way, the brake effect is restored.

The gear 26 is preferably a catalog item. In the actuator 24, a step motor may for example be integrated. The number of steps and the direction of rotation may be predetermined by a control electronics, for example an integrated circuit and/or a microprocessor. This way, also the duration of the release of the brake effect may be specified by software. Alternatively, also a DC motor may be used, which is controlled by signalers in the respective end position.

The bearing assembly 10 leverages an operation principle which provides the usage of cost efficient, easy to procure electric actuators 24, preferably small gear motors, and the usage of components which are cost-efficient to manufacture, in particular a high number of identical parts. In particular, the drive torque is to be increased in order to be able to use simple and cost-efficient gear motors. This is achieved in the present invention, for example, by means of the three transmission stages, wherein two are integrated in a double used mold part, that is the wedge elements 28, 32 of the adjustment device 22. The bearing assembly 10 provides a high degree of functional integration by using a few parts. Lifting of the respective coupling discs thus has not to be achieved by a magnetic force effect of an energized coil any more. The complex manufacturing of such a coil may be omitted. An engagement and disengagement of the coupling disc, which correspond here to the brake ring 40 and/or the upper lifting disc 32, may be realized by using a simple electric motor. Contrary hereto, a traditional coupling including a electromagnet is to be configured relative to a large air gap due to the distance required for the coupling feature, thus a strong and thus large electromagnet is required.

However alternatively, the adjustment device 22 may be used in order to directly achieve the pretension for generating the frictional force for inhibiting the movement of the two bearing elements 12, 14 of the bearing assembly 10 relative to each other.

The two wedge surfaces 34, 36 may also be configured as slopes, for example. In the present configuration, the actuator 24 is arranged outside of the bearing elements 12, 14. This way, it may be easily accessed for maintenance, and is not limited regarding the size thereof. The respective gearings of the two wedge elements 28, 32 may however be arranged radially inside, and thus the actuator 24 in a radial inner cavity of one of the bearing elements 12, 14. This way, the bearing assembly 10 may be especially small, and the actuator 24 is protected.

The bearing assembly 10 is especially advantageous for medical carrier arm systems, as different brake forces may be set for bearings having the same design. This way, it may be also effected that first a bearing assembly having a shorter lever arm starts to move due to the shorter carrier arm, and then a bearing assembly having a longer carrier arm. Thus it may be achieved for example that for a two-part carrier arm system including a long carrier arm which is mounted to a ceiling of surgery room, and a short carrier arm, which enables a fine-tuning directly next to the user, at first the short carrier arm may be adjusted without movement of the longer carrier arm at the ceiling. In addition, a provided brake force or frictional force, which inhibits the movement of the two bearing elements 12, 14 relative to one another, may be adjusted according to client requirements. In total, the bearing assembly 10 is thus cost efficient and robust.

FIG. 5 shows in a schematic partial section view a further embodiment of the bearing assembly 10, in which a brake disc 48 has been inserted instead of the brake ring 40, which acts on a bearing ring which is not coupled to the adjustment device 22. Correspondingly, the frictional element 20 may here be formed as a brake pad on a brake disc 48. This may for example be rotatably decoupled from the second bearing element 14 by means of a roller bearing 50, and be also pressed against the first bearing element 12 by means of an upper wedge element or the lifting disc 52.

LIST OF REFERENCE NUMBERS

10 Bearing assembly
12 First bearing element
14 Second bearing element
16 Longitudinal axis
18 Brake device
22 Frictional element
22 Adjustment device
24 Actuator
26 Gear
28 Lower wedge element
30 Gearing
32 Upper wedge element
34 Wedge surface
36 Wedge surface
38 Gearing
40 Brake ring
42 Spring element
44 Guiding pins
46 Elongated hole
48 Brake disc
50 Roller bearing
52 Lifting disc

The invention claimed is:

1. A bearing assembly comprising at least one first bearing element and one second bearing element which are rotatably connected relative to each other along a common longitudinal axis, wherein the bearing assembly comprises:
   a brake device which inhibits a relative rotation of the at least first and the at least second bearing elements to each other by a frictional force generated by the brake device; and
   an adjustment device by which a brake force acting during the relative rotation of the at least first and the at least second bearing elements to each other may be modified,
   wherein the adjustment device comprises at least two wedge elements which rest on respective wedge surface thereof on each other and which are movable in a sliding down manner against each other in order to modify the brake force, and
   wherein the at least two wedge elements are mounted to one of the at least first or the at least second bearing elements by a common guide.

2. The bearing assembly according to claim 1, wherein:
   the brake device comprises a first frictional surface which rotates with the at least first bearing element about the common longitudinal axis in a rotatably fixed way, and a second frictional surface which rotates with the at least second bearing element about the longitudinal axis (16) in a rotatably fixed way; and
   wherein the first and second frictional surfaces are clamped against each other by a pretension force and during rotation of the at least first and the at least second bearing elements relative to each other slide down against each other by generating the frictional force; and wherein the adjustment device is configured to modify said pretension force by moving the at least two wedge elements relative to each other in order to set the frictional force and thus modify the brake force.

3. The bearing assembly according to claim 1, wherein:
the bearing assembly comprises a coupling device which is adjustable between an open state and a closed state;
wherein in the closed state the brake device is engaged, whereby during a rotation of the at least first and the at least second bearing elements relative to each other, said rotation is inhibited by the frictional force generated by the brake device; and
wherein in the open state, the brake device is disengaged, whereby the at least first and the at least second bearing elements are rotatable relative to each other without being inhibited by the brake device; and
wherein the adjustment device is configured to adjust the coupling device between the open and closed states thereof by moving the at least two wedge elements relative to each other, and thus to modify the brake force.

4. The bearing assembly according to claim 1, wherein the adjustment device is configured such that by relative movement of the at least two wedge elements to each other, the at least two wedge elements optionally move towards each other or away from each other in a direction parallel to the common longitudinal axis.

5. The bearing assembly according to claim 1, wherein the at least two wedge elements are configured as identical parts.

6. The bearing assembly according to claim 1, wherein the wedge surfaces are clamped against each other on the wedge surfaces thereof by at least one spring element.

7. The bearing assembly according to claim 1, wherein at least one of the at least two wedge elements is configured as a ring element, which is rotatably arranged in order to move the at least two wedge elements relative to each other about the common longitudinal axis.

8. The bearing assembly according to claim 1, wherein the guide comprises a plurality of guide pins which are arranged around a periphery of the at least two wedge elements being formed as ring elements, and one of the at least two wedge elements is fixed to the guide pins in a rotatably fixed way, but axially movable relative to the common longitudinal axis.

9. The bearing assembly according to claim 1, wherein the adjustment device comprises an actuator by which the at least two wedge elements are movable relative to each other.

10. The bearing assembly according to claim 1, wherein at least one of the at least two wedge elements comprises a gearing which is engaged with a corresponding gearing of the actuator for moving said at least one of the at least two wedge elements.

11. The bearing assembly according to claim 7, wherein the at least two wedge elements are configured as ring elements.

12. The bearing assembly according to claim 1, wherein both of the at least wedge elements are attached to a corresponding one of the at least first and the at least second bearing elements, wherein one of the at least two wedge elements is arranged movably at least along an axial direction.

13. The bearing assembly according to claim 1, wherein at least one of the at least two wedge elements has a recess or a through hole for a wedge portion or the wedge surface of other of the at least two wedge elements.

14. The bearing assembly according to claim 8, wherein one of the at least two wedge elements is fixed by through holes matching to the guide pins in cross-sections thereof, and the other of the at least two wedge elements is fixed to the guide pins rotatably relative to the common longitudinal axis by respective elongated holes.

15. A bearing assembly comprising at least one first bearing element and one second bearing element which are rotatably connected relative to each other along a common longitudinal axis, wherein the bearing assembly comprises:
a brake device which inhibits a relative rotation of the at least first and the at least second bearing elements to each other by a frictional force generated by the brake device; and
an adjustment device by which a brake force acting during the relative rotation of the at least first and the at least second bearing elements to each other may be modified,
wherein the adjustment device comprises at least two wedge elements which rest on respective wedge surface thereof on each other and which are movable in a sliding down manner against each other in order to modify the brake force, and
wherein the at least two wedge elements are configured as identical parts.

16. A bearing assembly comprising at least one first bearing element and one second bearing element which are rotatably connected relative to each other along a common longitudinal axis, wherein the bearing assembly comprises:
a brake device which inhibits a relative rotation of the at least first and the at least second bearing elements to each other by a frictional force generated by the brake device; and
an adjustment device by which a brake force acting during the relative rotation of the at least first and the at least second bearing elements to each other may be modified,
wherein the adjustment device comprises at least two wedge elements which rest on respective wedge surface thereof on each other and which are movable in a sliding down manner against each other in order to modify the brake force, and
wherein the wedge surfaces are clamped against each other on the wedge surfaces thereof by at least one spring element.

17. A bearing assembly comprising at least one first bearing element and one second bearing element which are rotatably connected relative to each other along a common longitudinal axis, wherein the bearing assembly comprises:
a brake device which inhibits a relative rotation of the at least first and the at least second bearing elements to each other by a frictional force generated by the brake device; and
an adjustment device by which a brake force acting during the relative rotation of the at least first and the at least second bearing elements to each other may be modified,
wherein the adjustment device comprises at least two wedge elements which rest on respective wedge surface thereof on each other and which are movable in a sliding down manner against each other in order to modify the brake force, and wherein a guide comprises a plurality of guide pins which are arranged around a periphery of the at least two wedge elements being formed as ring elements, and one of the at least two wedge elements is fixed to the guide pins in a rotatably fixed way, but axially movable relative to the common longitudinal axis.

18. The bearing assembly according to claim 17, wherein one of the at least two wedge elements is fixed by through holes matching to the guide pins in cross-sections thereof, and the other of the at least two wedge elements is fixed to the guide pins rotatably relative to the common longitudinal axis by respective elongated holes.

* * * * *